(12) United States Patent
Dong et al.

(10) Patent No.: US 7,516,673 B2
(45) Date of Patent: *Apr. 14, 2009

(54) STRUCTURAL STRESS ANALYSIS

(75) Inventors: Pingsha Dong, Dublin, OH (US);
Jinmiao Zhang, Dublin, OH (US);
Jeong Kyun Hong, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 182 days.

This patent is subject to a terminal disclaimer.

(21) Appl. No.: 11/424,404

(22) Filed: Jun. 15, 2006

(65) Prior Publication Data

US 2006/0219026 A1 Oct. 5, 2006

Related U.S. Application Data

(60) Continuation of application No. 10/989,771, filed on Nov. 16, 2004, now Pat. No. 7,089,124, which is a division of application No. 09/992,552, filed on Nov. 16, 2001, now Pat. No. 6,901,809.

(60) Provisional application No. 60/249,800, filed on Nov. 17, 2000.

(51) Int. Cl.
*G01B 5/30* (2006.01)

(52) U.S. Cl. .............. 73/760; 73/804; 73/808

(58) Field of Classification Search ......... 73/760, 73/804, 808
See application file for complete search history.

(56) References Cited

U.S. PATENT DOCUMENTS

| | | | |
|---|---|---|---|
| 4,969,106 A | 11/1990 | Vogel et al. | |
| 5,437,190 A | 8/1995 | Ehrenpreis et al. | |
| 5,531,122 A | 7/1996 | Chatham et al. | |
| 5,616,866 A | 4/1997 | Murakami | |
| 5,841,033 A | 11/1998 | Burris et al. | |
| 5,841,040 A | 11/1998 | Walls | |
| 6,101,450 A | 8/2000 | Dasgupta | |
| 6,105,438 A | 8/2000 | Gieseke | |
| 6,125,333 A | 9/2000 | Pun | |
| 6,163,757 A | 12/2000 | Aizawa et al. | |
| 6,353,768 B1 | 3/2002 | Karafillis et al. | |
| 6,456,289 B1 | 9/2002 | O'Brien et al. | |
| 6,704,664 B2 * | 3/2004 | Su et al. ............... 702/34 |
| 6,781,702 B2 * | 8/2004 | Giannakopoulos et al. .. 356/601 |
| 6,904,395 B1 | 6/2005 | DeJack et al. | |
| 7,089,124 B2 * | 8/2006 | Dong et al. ............ 702/42 |
| 2002/0112548 A1 * | 8/2002 | Dong et al. ............ 73/850 |

(Continued)

OTHER PUBLICATIONS

W.F. Carroll; The Finite Element Method; A Primer for Finite Elements In Elastic Structures; 1991;34-43; John Wiley & Sons, Inc.

(Continued)

*Primary Examiner*—Max Noori
(74) *Attorney, Agent, or Firm*—Dinsmore & Shohl LLP

(57) ABSTRACT

Structural stress in a fatigue-prone region of a structure is determined and analyzed by using: i) the nodal forces and displacement values in the fatigue-prone region, or ii) equilibrium equivalent simple stress states consistent with elementary structural mechanics in the fatigue-prone region. Of course, it is contemplated that combinations, equivalents, or variations of the recited bases may alternatively be employed.

16 Claims, 10 Drawing Sheets

U.S. PATENT DOCUMENTS

2003/0106378 A1* 6/2003 Giannakopoulos et al. .... 73/788
2003/0114995 A1* 6/2003 Su et al. ................ 702/34
2005/0071091 A1* 3/2005 Dong et al. ............. 702/42
2006/0219026 A1* 10/2006 Dong et al. ............. 73/808

OTHER PUBLICATIONS

W.F. Carroll; Element Stiffness Equations by Direct Methods; A Primer for Finite Elements In Elastic Structures; 1991; 45, 50-61; John Wiley & Sons, Inc.

W.F. Carroll; General Approach to Element Stiffness Equations; A Primer for Finite Elements In Elastic Structures; 1991; 131-132; John Wiley & Sons, Inc.

W.F. Carroll; Structural Finite Elements In Perspective; A Primer For Finite Elements In Elastic Structures; 1991; 385-388; John Wiley & Sons, Inc.

Steve Owen; Mesh Generation: A Quick Introduction; 3 pages.

Mikael Fermer, Magnus Andreasson, and Bjorn Frodin; Fatigue Life Prediction of MAG-Welded Thin-Sheet Structures; 1998; 7 pgs. Sockety of Automotive Engineers, Inc.

Shicheng Zhang; Stress Intensities At Spot Welds; International Journal of Fracture; 1997; 167-185; Kluwer Academic Publishers; Netherlands.

Marcos L. Herrera and Richard A. Mattson; Alternate Methods for Evaluating Shroud Cracking Using Linear Elastic Fracture Mechanics Techniques; 8th International Conference on Nuclear Engineering; Apr. 2-6, 2000, Baltimer, MD 5 pgs.

Structural Integrity Associates, Inc.; Fracture Mechanics; Technical Literature; Dec. 1997, SIB-96-154, Rev. 1, 5 pgs.

Criteria of the ASME Boiler and Pressure Vessel Code for Design by Analysis in Sections III and VIII, Division 2; Design; pp. 61-83.

W.C. Kroenke; Classification of Finite Element Stresses According to ASME Section III Stress Categories; Nuclear Equipment Division; Bobcock & Wilcox, Akron, Ohiop; pp. 107-140: From: Pressure Vessel and Piping Technology—1985—A Decade of Progress, ASME.

* cited by examiner

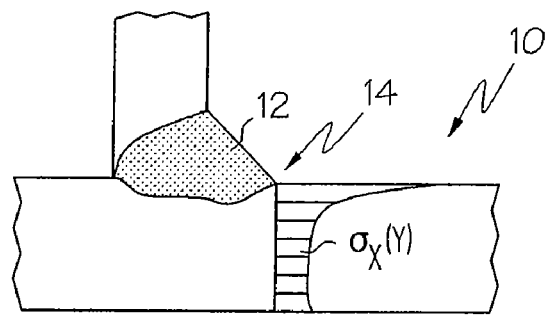
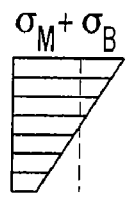
FIG. 1A
FIG. 1B
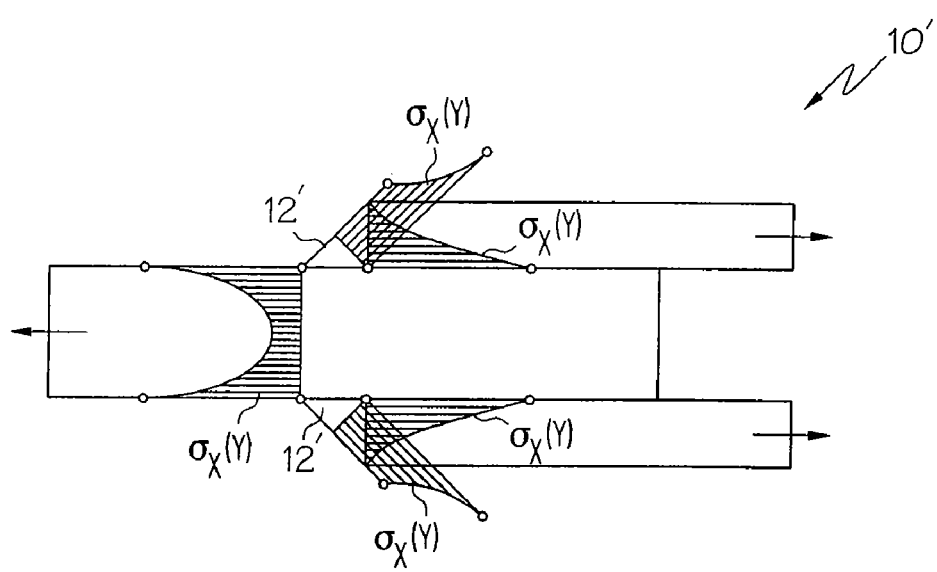
FIG. 1C
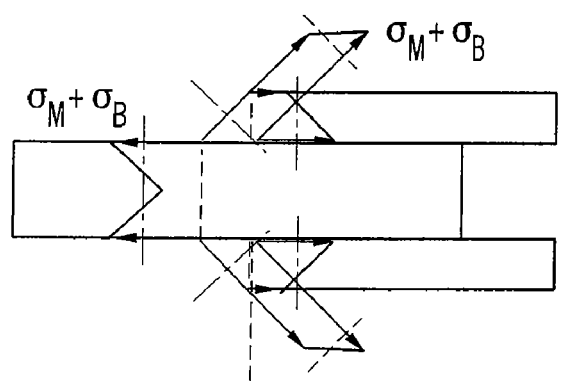
FIG. 1D

STRUCTURAL STRESS ANALYSIS

CROSS-REFERENCE TO RELATED APPLICATIONS

This application is a continuation of U.S. patent application Ser. No. 10/989,771, filed Nov. 16, 2004, which is a division of U.S. patent application Ser. No. 09/992,552, filed Nov. 16, 2001, which claims the benefit of U.S. Provisional Application Ser. No. 60/249,800, filed Nov. 17, 2000.

BACKGROUND OF THE INVENTION

The present invention relates to structural stress analysis and, more particularly to stress calculations and a scheme for calculating structural stress where the structure contains geometric discontinuities, e.g., welded joints, notches, ridges, bends, sharp corners, etc.

Stress analysis is used primarily in the design of solid structures such as ships, automobiles, aircraft, buildings, bridges, and dams for determining structural behavior and for ascertaining structural viability and integrity under anticipated or foreseeable loads. The analysis may involve the use of an abstract or mathematical model for the representation of the structural system and loads. According to classical analytical idealization, partial differential equations are used. For example, stress in a dam under a hydrostatic load can be described by an elliptic partial differential equation in two spatial dimensions.

As boundary geometry of structural systems is usually complicated, the partial differential equations of structural mechanics typically cannot be solved in the closed analytical exact form. Numerical approximations are sought instead. In one approach, derivatives are replaced with finite differences. Other methods are based on finding an approximation as a linear combination of preassigned functions such as polynomials or trigonometric functions. Also, after a domain or a boundary of interest has been discretized in the form of a large number of small elements, a piece-wise approximation can be sought according to the finite element method.

Current methods of stress analysis based upon numeric approximations and extrapolation are often subject to substantial uncertainties in regions of close proximity to welds, joints, sudden changes of geometry, or other structural or geometric discontinuities and are highly dependent on element size and are typically mesh dependent, particularly if drastically different loading modes are considered. Accordingly, there is a need for an improved structural stress analysis scheme for fatigue prediction that effectively eliminates or minimizes mesh dependency.

BRIEF SUMMARY OF THE INVENTION

This need is met by the present invention wherein structural stress in a fatigue-prone region of a structure is determined and analyzed by using: i) the nodal forces and displacement values in the fatigue-prone region, or ii) equilibrium equivalent simple stress states consistent with elementary structural mechanics in the fatigue-prone region. Of course, it is contemplated that combinations, equivalents, or variations of the recited bases may alternatively be employed. The determination is substantially independent of mesh size and is particularly well-suited for applications where S-N curves are used in weld fatigue design and evaluation, where S represents nominal stress or stress range and N represents the number of cycles to failure.

Throughout the present specification and claims certain quantities, functions, parameters, and values are described or identified as being determined, calculated, or measured. For the purposes of defining and describing the present invention, it is noted that the use of one of these terms herein is not intended to exclude steps that incorporate or may be defined with reference to another of the terms. For example, a "determination" may incorporate aspects that are measured or calculated, a "calculation" may depend upon a specific measurement or determination, and a measurement may be based upon a calculation or determination. The term "analysis" is utilized herein to refer to an identification, review, or examination of the results of a determination, calculation, measurement, or combination thereof.

For the purposes of defining and describing the present invention, it is noted that reference to a "mesh" or "grid" herein relates to the use of any defined reference framework for identifying, quantifying, or otherwise defining individual portions of an object or an actual or virtual model of an object. Typically, a single quantitative value is associated with individual points along the reference framework or with individual portions defined by the reference framework. A calculation that is mesh insensitive is substantially unaffected by the inherent precision, frequency, or definition of the reference framework. In stress/strain evaluation, it is common to utilize a finite element mesh derived by dividing a physical domain into smaller sub-domains or elements in order to facilitate a numerical solution of a partial differential equation. Surface domains may be subdivided into triangle or quadrilateral shapes, while volumes may be subdivided primarily into tetrahedral or hexahedral shapes. The size, shape and distribution of the elements is ideally defined by automatic meshing algorithms.

The present invention is directed to a structural stress calculation scheme that generates stress determinations that are substantially independent of the size, shape and distribution of the mesh elements. Validations of the stress analysis scheme of the present invention reveal that structural stress determined according to the present invention proved to be substantially independent of mesh size over at least the following mesh size ranges: (i) from about 0.16 t and 0.1 t, along respective x and y axes, to about 2 t and t along respective x and y axes; (ii) from about 0.5 t and t, along respective x and y axes, to about 2 t and t along respective x and y axes; and (iii) from about 0.008 t and 0.02 t, along respective x and y axes, to about 0.4 t and 0.5 t along respective x and y axes, where t represents the thickness of the structure. For the purposes of defining the present invention, it is noted that claims reciting a mesh are intended to cover any reference framework, like a mesh, grid, or other framework, where a domain is divided into sub-domains or elements.

The present invention has application to stress evaluation of a variety of welded and non-welded joints, notches, ridges, bends, sharp corners, and other discontinuities or sudden changes in geometry in metallic, plastic and ceramic structures. Relevant structures include aircraft and aerospace equipment (aircraft, helicopters, rockets, gantries); agricultural equipment (aerators, balers, baggers, choppers, combines, cultivators, elevators, feeders, grain hoppers, bins and sorters, harrows, harvesters, mowers, mulchers, planters, plows, scrapers, seeders, shredders, sprayers, spreaders, tillers, threshers, tractors); agricultural structures (silos, barns, brooders, incubators); automobiles and trucks (automobiles, trucks, trailers, wagons, axles, hitches); construction and lifting equipment (bulldozers, cranes, hoists, winches, jacks, chains, spreaders, hi-los, backhoes, forklifts, loaders, haulers, scrapers, excavators, graders, trenchers, borers, directional drillers, pulverizers, saws); forestry equipment (skidders, feller bunchers, log loaders, log splitters); mining equipment; rail car frames; ships; submarines and submersibles; ports and port equipment (docks, piers, cranes, lighthouses); bridges (bridges, bridge expansion joints); channels or canals; tunnels; building components (doors, door frames, windows, sashes, shutters, soffits, fascia, skylights, scaffolding, cabinetry, chimneys and flues, elevators); building materials (framing channels and struts, joists, trusses and truss plates, wire reinforced concrete); appliances, home and industrial (sinks, stoves, ovens, refrigerators, baths); buildings/skyscrapers (steel decks, mezzanines); housing, particularly manufactured or modular; heating and cooling systems (especially ducts); home improvement equipment (ladders, hand tools); fencing and gates; plumbing (pipes, fittings, pumps, sewage lines); irrigation and drainage equipment (pipes, irrigation sprinkler systems, drains and drainpipes); manufacturing equipment and machinery (conveyors, fasteners, riveters); diving equipment; nuclear containers and facilities; offshore oil rigs; diesel and gas turbines; pipelines; derricks and digger derricks; cooling towers; radio towers/transmitters; welded structures (welded wire reinforcements); tanks and cisterns (esp. for water storage); aircraft components; automotive parts; footwear; household components (sinks, showers, plumbing pipe, swimming pools); sporting goods; ceramics; concrete; porcelain enamel; sealants and sealed structures, adhesively bonded structures; etc.

The stress analysis scheme of the present invention may also be utilized to monitor stress, predict failure, schedule maintenance, determine fatigue, and analyze structures. The structural stress analysis scheme of the present invention is particularly significant in these contexts because a 10% variation in a stress value could translate into a life cycle that varies by as much as 100-200%. Further, the stress analysis scheme of the present invention may be utilized as a structural design tool directed at optimizing manufacturing costs or as a tool for monitoring, locally or remotely, structural stress in situ or during manufacture or assembly to guide manufacturing or assembly steps. Structures may be analyzed by imaging the structure, creating a model of the structure and applying the principles of the present invention to assess the stress in the structure. It is contemplated that the scheme of the present invention may be incorporated into an otherwise conventional, field-ready hand-held or desk top computer or programmable device.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which:

FIGS. 1A, 1B, 1C, and 1D illustrate typical welded joints and corresponding structural stress definitions and local stress distributions associated therewith;

DETAILED DESCRIPTION

Figure 2A:
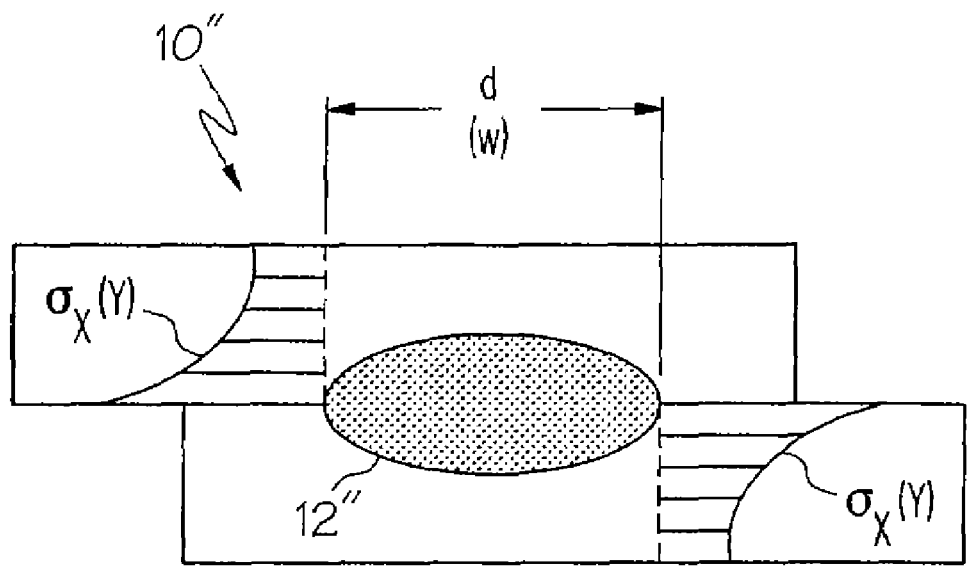
FIGS. 2A and 2B illustrate structural stress definitions and local stress distributions associated with spot and laser lap joints.

The following detailed description is presented according to the following subject matter outline, as delineated in the body of the description:
1. Structural Stress Analysis by Enforcing Equilibrium Conditions and solving for $\sigma_B$, and $\sigma_M$
1.1. Stress Analysis by Using Stress Distributions $\sigma_x(y)$ and $\tau_{xy}(y)$.
1.2. Stress Analysis by Using Stress Resultants.
1.3. Special Applications—Partial Thickness Fatigue Crack.
1.4. Special Applications—Non-Monotonic Through-Thickness Distributions.
2.0. Calculation of Structural Stress by Conversion of Nodal Forces and Moments.
2.1. Conversion of Nodal Forces and Moments Retrieved Directly from Shell Model.
2.2. Conversion of Nodal Forces and Moments by Generating Stiffness Matrices and Nodal Displacements from the Shell Model.
2.3. Conversion of Nodal Forces and Moments from Three-Dimensional Solid Model.
3. Experimental Techniques for Measuring Structural Stress
3.1. Monotonic Through-Thickness Distributions
3.2. Non-monotonic Through-Thickness Stress Distributions Referring initially to FIGS. 1A, 1B, 1C and 1D, it is noted that structures containing geometric discontinuities generally possess localized stress concentrations and corresponding through-thickness stress distributions. For example, the structure or plate 10 illustrated in FIG. 1A includes a fillet weld 12 and defines a particular through-thickness stress distribution $\sigma_x(y)$. The stress distribution $\sigma_x(y)$ is defined along a cross section of the structure 10 in a fatigue-prone region or weld toe 14 of the weld 12 and may be obtained, for example, from a finite element model of the structure 10. FIG. 1B illustrates the corresponding structural stress definition in terms of two components $\sigma_M$, $\sigma_B$ of the structural stress $\sigma_s$ in the localized fatigue-prone region 24. The structural stress definition illustrated in FIG. 1B is effectively a simple structural stress distribution in the form of membrane and bending components $\sigma_M$, $\sigma_B$ that are equilibrium-equivalent to the local stress distributions in FIG. 1A.

Through-thickness stress distributions $\sigma_x(y)$ with respect to potential failure planes for a structure 10' including lap fillet joints 12' are illustrated in FIG. 1C. In such joint types, depending on actual geometry and loading conditions, three possible fatigue-prone regions or failure planes exist: (1) weld root failure along the weld throat; (2) weld toe failure; and (3) weld root/toe failure. The through-thickness stress distributions $\sigma_x(y)$ correspond to cross sections of the structure 10' taken along the different fatigue-prone regions of the structure 10'. The corresponding equilibrium-equivalent simple structural stress definitions are illustrated in FIG. 1D in terms of the two components $\sigma_M$, $\sigma_B$ of the structural stress $\sigma_s$ in the different fatigue-prone regions.

Figure 2B:
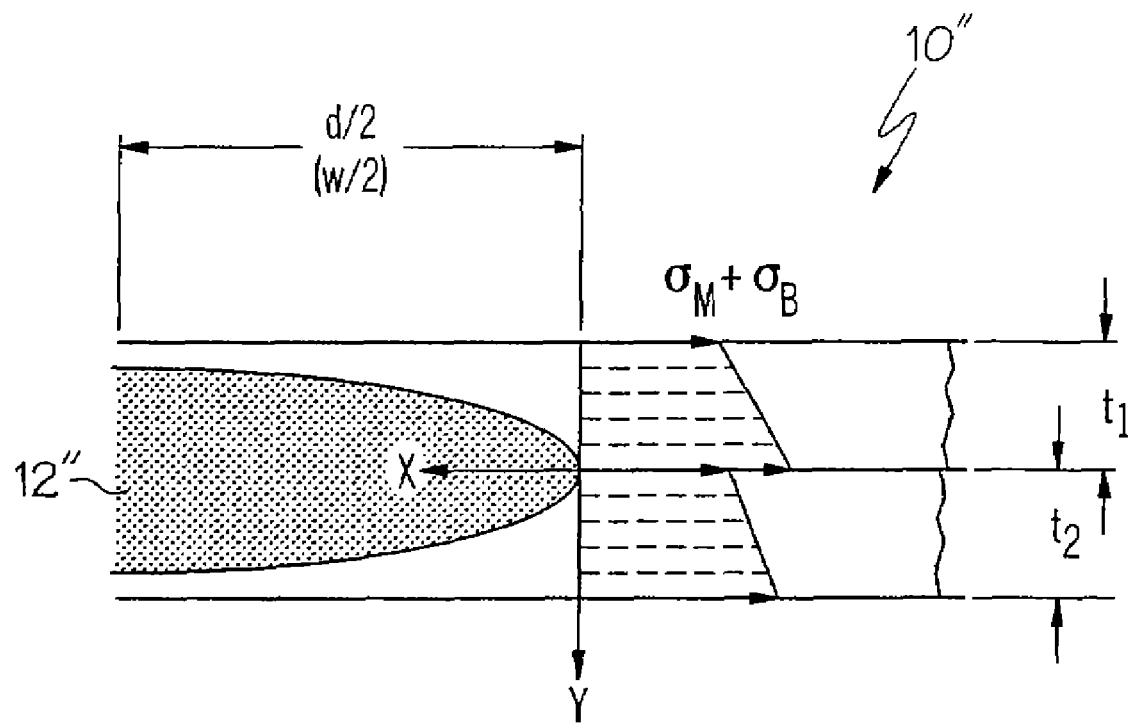

Referring now to FIGS. 2A and 2B, local normal stress distributions $\sigma_x(y)$ along a typical failure plane are illustrated for structures 10" including a spot weld 12" (e.g., a resistance spot weld) or a laser lap weld 12"'. Regardless of whether the structure 10" includes a laser lap weld or resistance spot weld, the local normal stresses and structural stresses are essentially defined the same. Note that for resistance spot welds, see FIG. 2A, both the local stresses and the structural stresses are a function of circumferential angle. In the case of typical laser lap welds, see FIG. 2B. In the case of a laser lap weld, the weld area will occupy the entire cross-section without the half-width (w/2). If the stress quantities can be adequately defined in the x-y plane of FIG. 2B despite the fact that the long lap joint extends in a direction orthogonal to the x-y plane.

Figure 4:
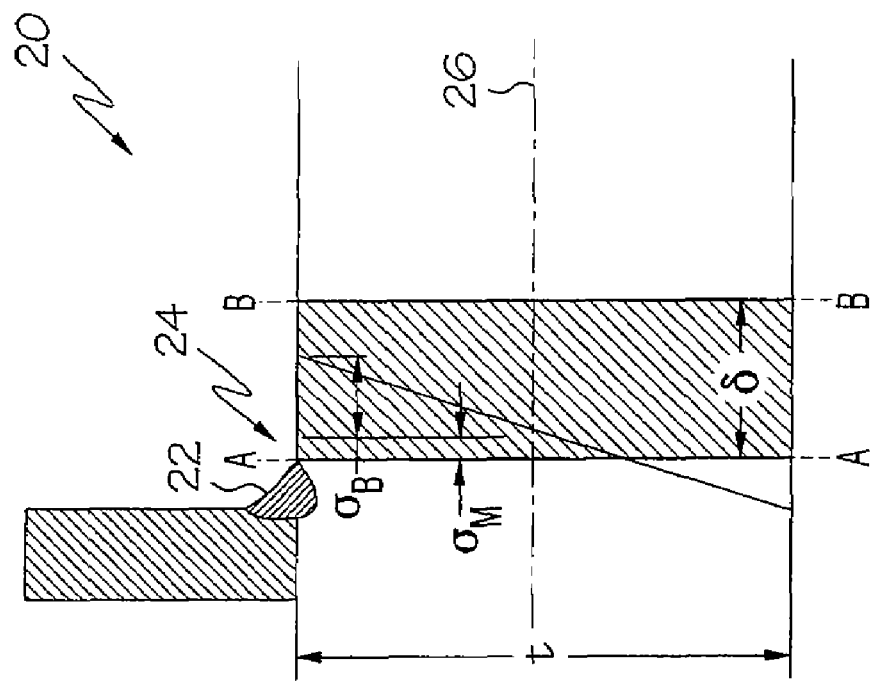
FIG. 4 represents a structural stress definition, taken along section line A-A, corresponding to the normal and shear stress distributions of FIG. 3.
Figure 3:
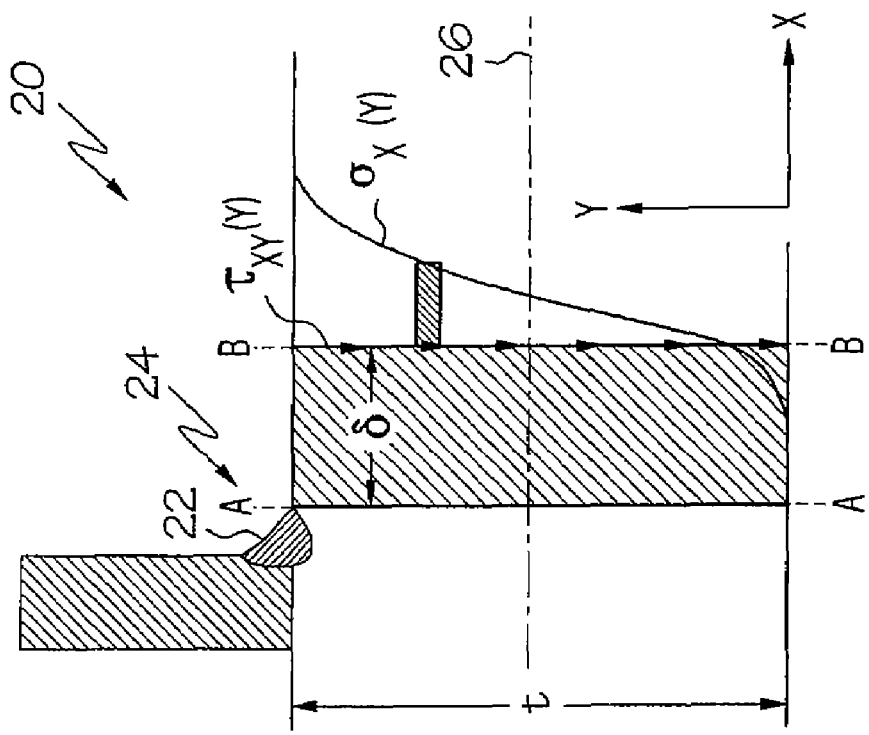
FIG. 3 illustrates normal and shear stress distributions from a typical finite element model at a reference cross section of a structure for structural stress calculations.

FIG. 3 illustrates in further detail the local normal stress distribution $\sigma_x(y)$ and the shear stress distribution $\tau_{xy}(y)$ of a structure 20 or, more specifically, a structural member 20, in a fatigue-prone region 24 in the vicinity of a weld 22 of the structure 20. The values of $\sigma_x(y)$ and $\tau_{xy}(y)$ are taken along line B-B of FIG. 3 for calculation purposes only. The value of t corresponds to the thickness of the structure 20 in the selected cross section. The structural mid-plane 26 is illustrated in FIGS. 3 and 4. FIG. 4 represents a structural stress definition corresponding to $\sigma_x(y)$ and $\tau_{xy}(y)$ along section A-A of FIG. 3 and includes, more particularly, the two components $\sigma_M$, $\sigma_B$ of the structural stress $\sigma_s$ in the localized fatigue-prone region 24. Also illustrated in FIGS. 3 and 4 is the variable $\delta$ which represents the finite element size of a finite element model utilized in calculating structural stress according to the present invention. Typically, a single element row corresponds to the distance between sections A-A and B-B. It is noted that $\sigma_B$ assumes a value of zero at the structural mid-plane 26.

1. Structural Stress Analysis by Enforcing Equilibrium Conditions and solving for $\sigma_B$, and $\sigma_M$ A finite element model of a structure can be used to retrieve either stress outputs or nodal forces and displacements of the structure. If nodal forces and displacements are retrieved from the model, they can be used to calculate structural stresses in an accurate manner. In using two and three-dimensional solid element models, it can be more convenient to retrieve stress outputs directly from the finite element model. Stress outputs retrieved in this manner must, however, be processed by enforcing equilibrium conditions at a reference location in the structure.

According to the methodology of one embodiment of the present invention, structural stress $\sigma_s$ in a localized fatigue-prone region of a structure (e.g., section A-A of FIGS. 3 and 4) is defined in terms of the bending and membrane components $\sigma_B$, $\sigma_M$ of the structural stress $\sigma_s$ in the region. The structural stress is calculated by enforcing equilibrium conditions in the region and performing a selected integration utilizing stress distributions $\sigma_x(y)$ and $\tau_{xy}(y)$ derived from an established source, such as a finite element model.

As will be appreciated by those practicing the present invention, finite element models of a variety of structures have been, and may be, generated through computer-aided engineering. These finite element models may be used to derive individual stresses or internal loads for an area of interest within the structure. Accordingly, the stress distributions $\sigma_x(y)$ and $\tau_{xy}(y)$ are typically derived from a finite element model and are described herein in the context of finite element models. It is important to note, however, that the stress distributions may be derived or input from any of a variety of sources, either existing or yet to be developed. For example, a number of finite difference models and so-called meshless calculation systems are currently under development for structural stress modeling.

The structural stress distribution $\sigma_x(y)$ must satisfy equilibrium conditions within the context of elementary structural mechanics theory at both the hypothetical crack plane (e.g., at weld toe 14 in FIG. 1A) and a nearby reference plane, on which local stress distributions are known a priori from typical finite element solutions. The uniqueness of such a structural stress solution can be argued by considering the fact that the compatibility conditions of the corresponding finite element solutions are maintained at this location in such a calculation.

It should be noted that in typical finite element based stress analysis, the stress values within some distance from the weld toe can change significantly as the finite element mesh design changes. This behavior is referred to herein as mesh-size sensitivity. While local stresses near a notch are mesh-size sensitive due to the asymptotic singularity behavior as a notch position is approached, the imposition of the equilibrium conditions in the context of elementary structural mechanics according to the present invention eliminates or minimizes the mesh-size sensitivity in structural stress calculations. This is due to the fact that the local stress concentration close to a notch is dominated by self-equilibrating stress distribution.

1.1. Stress Analysis by Using Stress Distributions $\sigma_x(y)$ and $\tau_{xy}(y)$.

According to one method of the present invention, a cross section of interest (e.g., section B-B of FIGS. 3 and 4), the location of which is defined by a unit width, is selected such that the localized, fatigue-prone, region lies adjacent to the selected cross section. For the purposes of describing and defining the present invention, it is noted that elements that are separated by a single element distance from a selected cross section are said to lie adjacent to the cross section.

A first component $\sigma_M$ of the structural stress $\sigma_s$ in the localized region (e.g., section A-A of FIGS. 3 and 4) represents what may be referred to as a membrane component of the structural stress $\sigma_s$. A second component $\sigma_B$ of the structural stress $\sigma_s$ in the localized region represents what may be referred to as a bending component of the structural stress $\sigma_s$. The structural stress $\sigma_s$ is calculated by combining the first component $\sigma_M$ of the structural stress and the second component $\sigma_B$ of the structural stress as follows:

$$\sigma_s = \sigma_M + \sigma_B$$

By imposing equilibrium conditions between Sections A-A and B-B, the structural stress components $\sigma_m$ and $\sigma_b$ may be determined according to the following equations. Specifically, the first component $\sigma_M$ of the structural stress as in the localized region is determined according to the following equation:

$$\sigma_M = \frac{1}{t}\int_0^t \sigma_x(y)\,dy$$

The stress distribution $\sigma_x(y)$ along the selected cross section represents the local structural through-thickness stress distribution and is determined from the finite element model of the structure. The second component $\sigma_B$ of the structural stress as in the localized region is determined by solving the following equation for $\sigma_B$:

$$\left(\frac{t^2}{2}\right)\sigma_M + \left(\frac{t^2}{6}\right)\sigma_B = \int_0^t \sigma_x(y)y\,dy + \delta\int_0^t \tau_{xy}(y)\,dy$$

The term y corresponds to a distance along the y-axis from y=0 to a material point of interest in the selected cross section. The term t corresponds to the thickness of the structure in the selected cross section and $\delta$ represents the element size of the finite element model. The function $\tau_{xy}(y)$ represents the shear stress distribution and is determined from the finite element model of the structure. It is contemplated that, in practice, a row of elements may be used between the localized fatigue-prone region of a structure (e.g., section A-A of FIGS. 3 and 4) and the selected cross section (e.g., section B-B of FIGS. 3 and 4).

The equation for the first component $\sigma_M$ of the structural stress $\sigma_s$ represents the force balances in the x direction, evaluated along B-B. The equation for the second component $\sigma_B$ of the structural stress $\sigma_s$ represents the moment balances with respect to Section A-A at y=0. The integral term on the right hand side of the equation for the second component $\sigma_B$ represents the transverse shear force as a component of the structural stress definition. Accordingly, it is noted that, under certain conditions, such as if the transverse shear effects are not significant or if the finite element formulation provides adequate consideration of shear locking effects (particularly when using relatively large size elements), the structural stresses can be calculated directly from section A-A as follows:

$$\sigma_M = \frac{1}{t}\int_0^t \sigma_x(y)\,dy$$

$$\left(\frac{t^2}{2}\right)\sigma_M + \left(\frac{t^2}{6}\right)\sigma_B = \int_0^t \sigma_x(y)y\,dy$$

1.2. Stress Analysis by Using Stress Resultants.

Figure 10:
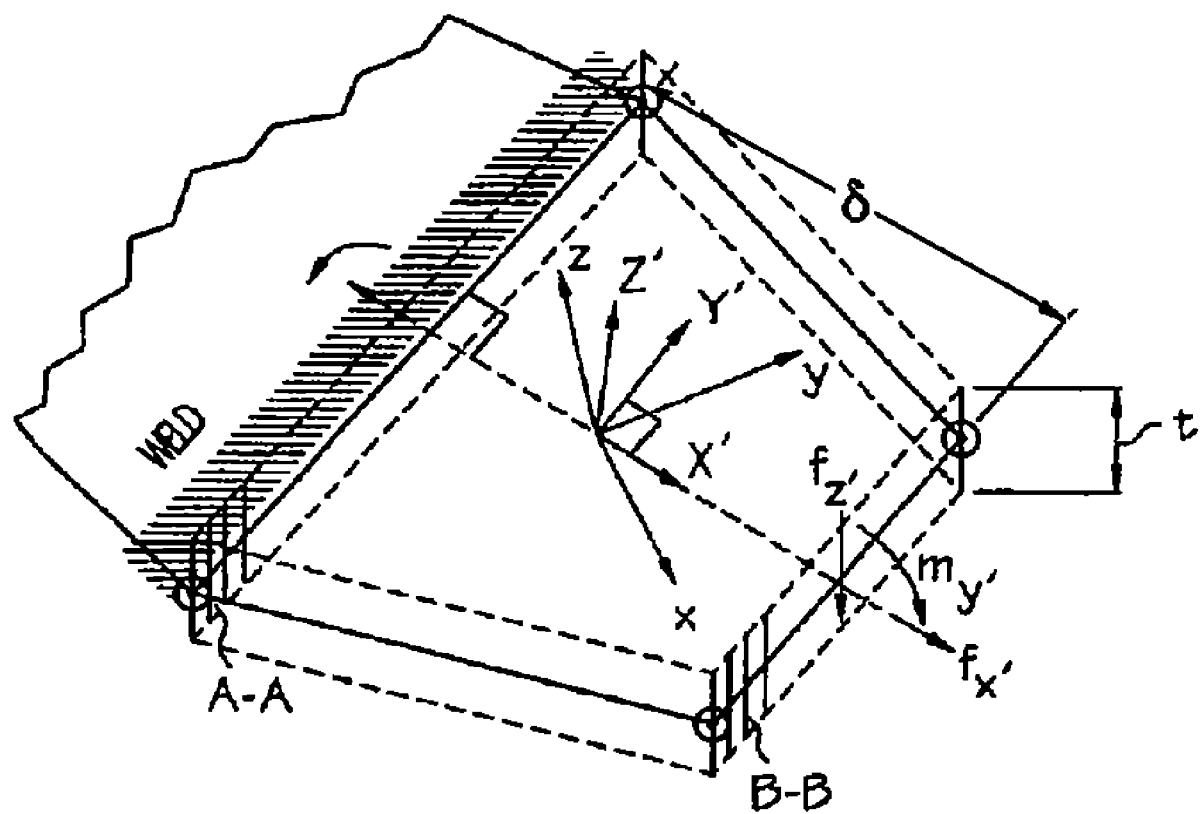
FIG. 10 illustrates a scheme for analyzing structural stress by utilizing stress resultants directly available from finite element codes or another source of similar data.

Referring briefly to FIG. 10, stresses and nodal quantities from shell or plate finite element models are often defined in a global coordinate system (x, y, z), depending on the finite element codes used. Given the definition of the structural stress components in Eq. 1, it is the local coordinate system (x',y',z') that is convenient for calculating the structural stresses with respect to a weld, with local x' and y' being perpendicular and parallel to the weld direction, respectively. Consistent with the solid element model approach (e.g., see FIG. 3), three components of the stress resultants (sectional forces and moments), i.e., $f_{x'}$, $f_{z'}$, and $m_{y'}$, at Section B-B in FIG. 10 can be used to calculate the structural stress components at Section A-A: it is noted that structural stress may also be analyzed by utilizing stress resultants directly available from finite element codes or another source of similar data. Specifically, three components of the stress resultants $f_{x'}$, $f_{z'}$, and $m_{y'}$ in at Section B-B in FIG. 10 can be used to calculate the structural stress components at Section A-A according to the following equation:

$$\sigma_s = \sigma_M + \sigma_B = \frac{f_{x'}}{t} + \frac{6(m_{y'} + \delta f_{z'})}{t^2}$$

where $\delta$ and t represent the dimensional values illustrated in FIG. 10 and $f_{x'}$, $f_{z'}$, and $m_{y'}$ represent the stress resultants illustrated in FIG. 10.

According to this aspect of the present invention, a finite element formulation with six degrees of freedom at each node is assumed, i.e., six components of generalized forces at each node (three translational and three rotational). If stresses in the global coordinate system are used, they must be transformed to the local coordinate system before structural stress is calculated in the manner described above.

1.3. Special Applications—Partial Thickness Fatigue Crack.

Figure 5A:
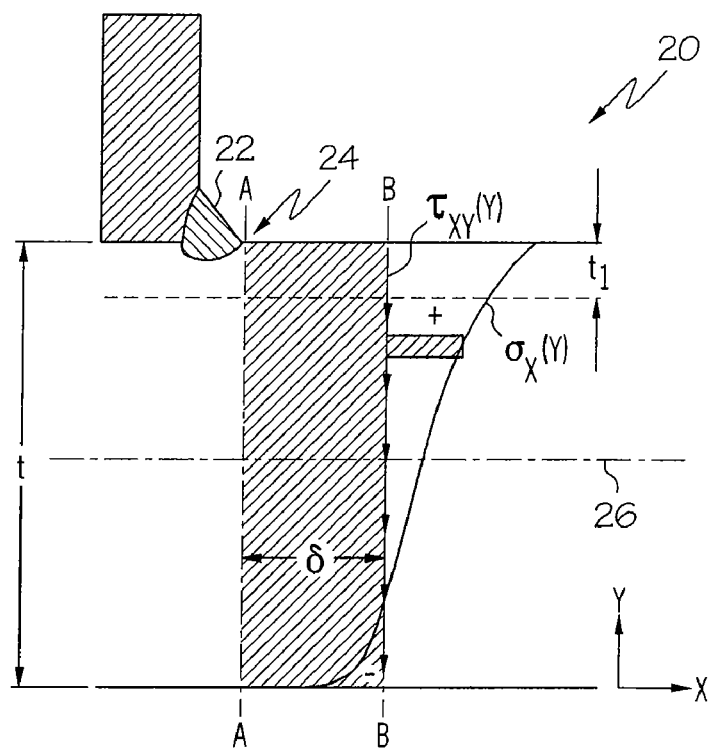
FIG. 5A illustrates local normal stress and shear stress distributions at a reference cross-section for a fatigue failure criterion corresponding to a structure including partial thickness fatigue crack.
Figure 5B:
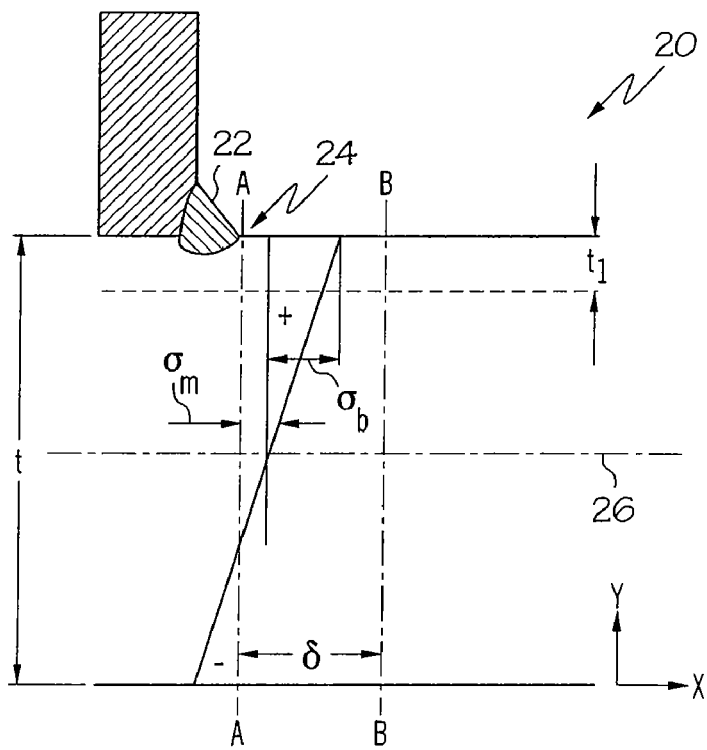
FIG. 5B represents the structural stress definition relative to the overall thickness of the structure of FIG. 5A.
Figure 5C:
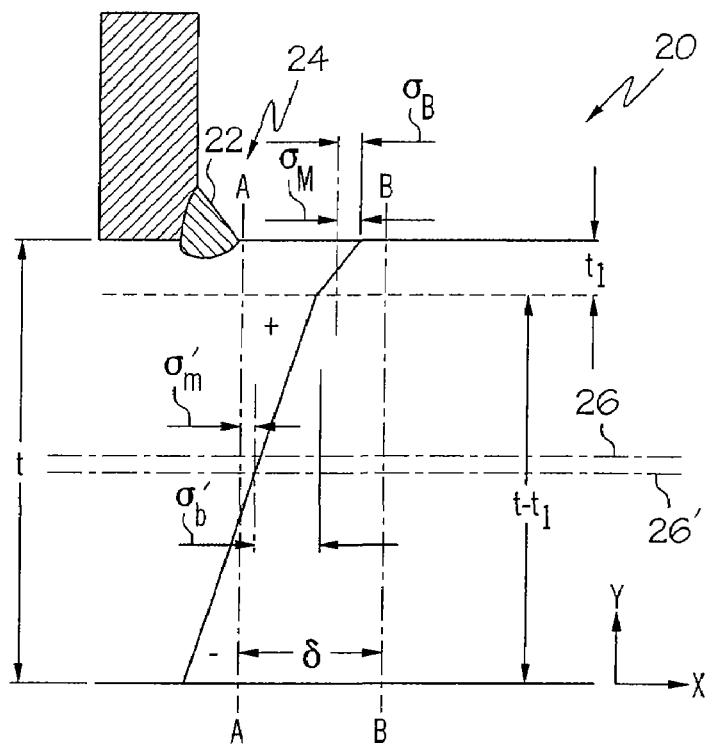
FIG. 5C represents the structural stress definition for the structure of FIG. 5A with a partial thickness fatigue crack failure.

Referring to FIGS. 5A, 5B, and 5C, an alternative scheme is described herein for calculating structural stress $\sigma_s$ where the selected cross section of the structure at issue includes a partial thickness fatigue crack extending a distance $t_1$ below a surface of the structure. According to this alternative scheme, the stress calculation scheme discussed above with respect to FIGS. 3 and 4, is altered by introducing two additional structural stress parameters $\sigma_m'$ and $\sigma_b'$ to enable the calculation of structural stress $\sigma_s$ where the selected cross section of the structure at issue includes the partial thickness fatigue crack extending a distance $t_1$ below a surface of the structure 20. The parameters $\sigma_m'$ and $\sigma_b'$ are illustrated in FIG. 5C. The overall through-thickness structural stress components $\sigma_m$ and $\sigma_b$, illustrated in FIG. 5B, are calculated as discussed above with respect to the components $\sigma_M$ and $\sigma_B$ of FIGS. 3 and 4. For the scheme of FIGS. 5A, 5B, and 5C, the structural stress $\sigma_s$ is calculated by combining a redefined first component $\sigma_M$ of the structural stress and a redefined second component $\sigma_B$ of the structural stress as follows:

$$\sigma_s = \sigma_M + \sigma_B$$

According to this alternative scheme, the first and second components $\sigma_M$, $\sigma_B$ of the structural stress $\sigma_s$ in the localized region, with respect to $t_1$ are determined by solving a first equation through direct integration and by solving simultaneously three equations with three unknowns.

A first equation of the four equations defines the sub-component $\sigma_m'$ of the structural stress $\sigma_s$. A second equation of the four equations defines a force equilibrium condition. A third equation of the four equations defines a moment equilibrium condition. A fourth equation of the four equations defines a stress continuity condition.

Regarding the first equation, since $\sigma_m'$ is not mesh-size sensitive, it can be calculated by direct integration along B-B within the length of $t-t_1$ as follows:

$$\sigma'_M = \frac{1}{t-t_1}\int_0^{t-t_1} \sigma_x(y)\,dy - \frac{1}{t-t_1}\int_0^{\delta} \tau_{yx}(x)\,dx$$

where $\sigma_m'$ and $\sigma_b'$ comprise respective sub-components of the structural stress $\sigma_s$ and are taken relative to a reference line 26' of the structure 20. The position of the reference line 26' corresponds to the centroid or neutral axis of the region defined between $t=0$ and $t=t-t_1$. The structural mid-plane 26 is also illustrated.

By enforcing force balances along x and y, and moment balance at $y=0$ at Section A-A, the second, third, and fourth equations are available. The second equation, defining the force equilibrium condition along the x-axis, is as follows:

$$\sigma_M t_1 + \sigma_m'(t-t_1) = \sigma_m t.$$

The third equation, defining the moment equilibrium condition is as follows:

$$(\sigma_M - \sigma_B)t_1\left(t - \frac{t_1}{2}\right) + \sigma_B t_1\left(t - \frac{t_1}{3}\right) + \sigma_m'\frac{(t-t_1)^2}{2} + \sigma_b'\frac{(t-t_1)^2}{6} = \sigma_m\left(\frac{t_1^2}{2}\right) + \sigma_b\left(\frac{t_1^2}{6}\right).$$

The fourth equation, defining the stress continuity condition at $y=t-t_1$ is as follows:

$$\sigma_M - \sigma_B = \sigma_m' + \sigma_b'$$

These three additional equations, defining three unknowns ($\sigma_M$, $\sigma_B$, $\sigma_b'$), may be solved simultaneously, according to conventional methods, to determine the values of the first and second components $\sigma_M$, $\sigma_B$ of the structural stress $\sigma_s$ in the localized region.

1.4. Special Applications—Non-Monotonic Through-Thickness Distributions.

Figure 6A:
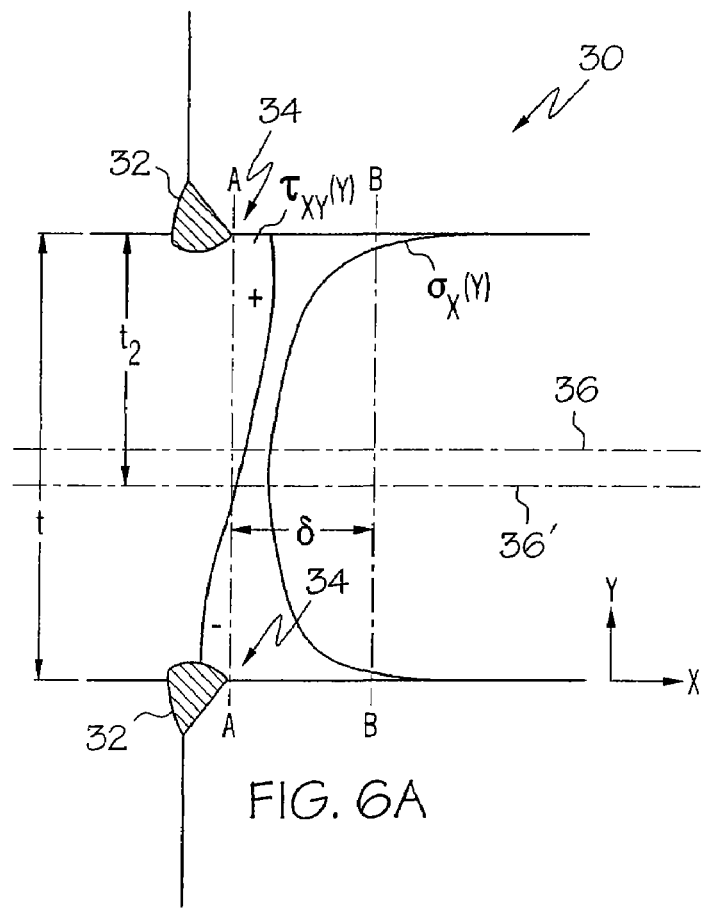
FIG. 6A illustrates local normal and shear stress distributions of a structure defining a non-monotonic through thickness stress distribution at a weld toe of the structure.
Figure 6C:
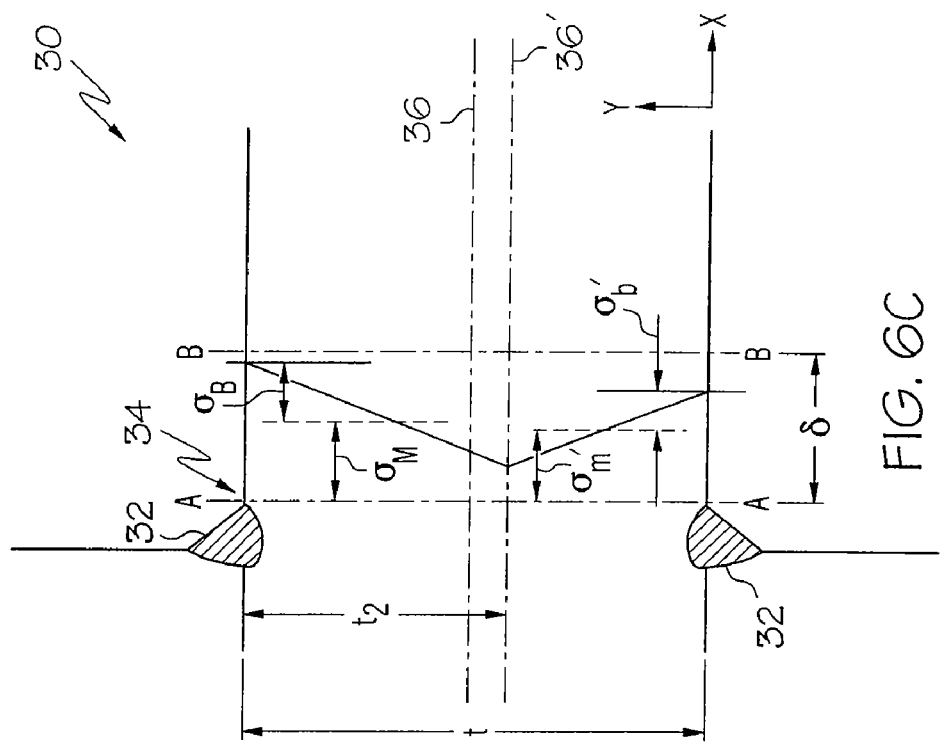
FIG. 6C illustrates structural stress components relative to both upper and lower portions of the structure illustrated in FIG. 6A.
Figure 6B:
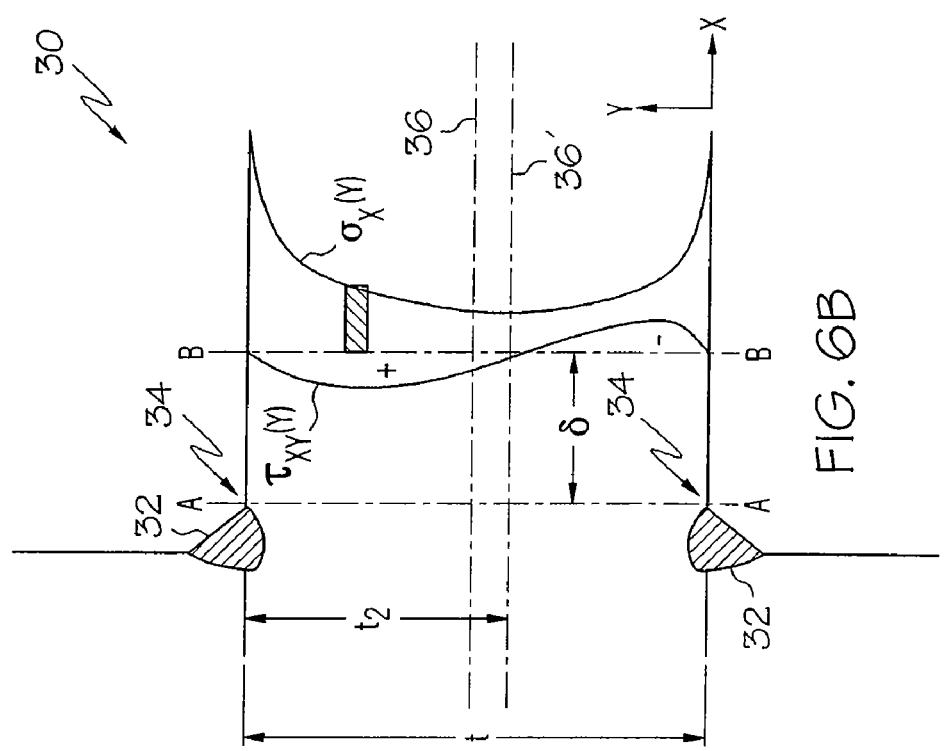
FIG. 6B illustrates respective local normal and shear stress distributions at a reference section of the structure illustrated in FIG. 6A.

Referring now to FIGS. 6A, 6B, and 6C, a process for calculating structural stress in a localized fatigue-prone region of a structure 30 defining a non-monotonic through thickness stress distribution is illustrated. The structure 30 includes a pair of welds 32 defining weld toes 34 and is merely illustrated partially and schematically in FIGS. 6A, 6B, and 6C. FIG. 6A illustrates local normal and shear stress distributions of the structure 30 at the weld toe 34 of the structure 30. FIG. 6B illustrates respective local normal $\sigma_x(y)$ and shear $\tau_{xy}(y)$ stress distributions at a reference section of the structure 30. FIG. 6C illustrates structural stress components relative to both upper and lower portions of the structure 30.

The stress distribution $\sigma_x(y)$ of FIGS. 6A and 6B defines a minimum axial stress along a secondary axis 36' of the structure 30 where the transverse shear stress distribution $\tau_{xy}(y)$ changes signs. The secondary axis 36' of the structure lies a distance $t_2$ below a surface of the structure 30. The structural mid-plane 36 is also illustrated in FIGS. 6A, 6B, and 6C. The cross-section references A-A and B-B are similar to those described above with reference to FIGS. 3 and 4. The parameter $t_2$ can be determined based on the position at which the transverse shear stress changes direction, if there is no specified crack depth as a failure criterion.

Two additional structural stress parameters $\sigma_m'$ and $\sigma_b'$ are illustrated in FIG. 6C. FIG. 6C illustrates these further sub-components $\sigma_m'$ and $\sigma_b'$ of structural stress $\sigma_s$ taken relative to the secondary axis 36' of the structure 30. FIG. 6C also illustrates the two primary components $\sigma_M$ and $\sigma_B$ of the structural stress $\sigma_s$ where $$\sigma_s = \sigma_M + \sigma_B$$

and where the stress continuity condition at $y=t-t_2$ is as follows:

$$\sigma_M - \sigma_B = \sigma_m' + \sigma_b'$$

FIG. 6C also illustrates the structural stress definitions corresponding to the non-monotonic through-thickness stress distribution illustrated in FIG. 6A. If the stress distribution $\sigma_x(y)$ is symmetric with respect to the mid-plane 36 of the structural member 30, then $t_2=t/2$; and the reference plane 36' coincides with the mid-plane 36. Generally, $\sigma_M$, $\sigma_B$, $\sigma_b'$, and $\sigma_m'$ can be solved in a manner similar to the scheme illustrated above with respect to the embodiment of FIGS. 5A, 5B, and 5C, provided $t_2$ has been determined. The parameter $t_2$ can be determined either by considering equilibrium conditions with respect to the entire through-thickness section (t) or, more conveniently, by identifying the point at which the transverse shear stress distribution $\tau_{xy}(y)$ changes signs, as is also discussed above with reference to the location of the structural mid-plane 26 of FIG. 5B.

Where the top surface of the structure 30 corresponds to the location of the maximum structural stress, the structural stress $\sigma_s$ in the localized region may be calculated by solving simultaneously the following equations for the two unknowns, $\sigma_M$, $\sigma_B$:

$$\sigma_M = \frac{1}{t_2}\int_{t-t_2}^{t} \sigma_X(y)\,dy$$

$$\left(\frac{t_2^2}{2}\right)\sigma_M + \left(\frac{t_2^2}{6}\right)\sigma_B = \int_{t-t_2}^{t} \sigma_X(y)y\,dy + \delta\int_{t-t_2}^{t} \tau_{xy}(y)\,dy$$

The two additional structural stress parameters $\sigma_m'$ and $\sigma_b'$ can be calculated according to the following equations:

$$\sigma_m' = \frac{1}{t-t_2}\int_0^{t-t_2} \sigma_X(y)\,dy$$

$$\sigma_m'\frac{(t-t_2)^2}{2} + \sigma_b'\frac{(t-t_2)^2}{6} = \int_0^{t-t_2} \sigma_X(y)y\,dy + \delta\int_0^{t-t_2} \tau_{xy}(y)\,dy$$

For the calculation of structural stress for resistance spot and laser lap welds (see FIGS. 2A and 2B), if two or three-dimensional solid element models are used, the calculation procedures are similar to the procedures described above with reference to FIG. 4. The fatigue crack typically initiates at the weld edge at the interface between the two sheets, where structural stress peak is located. A special case arises where the joint configuration and loading are symmetric with respect the neutral axis. In this case, the shear stress on the cross section along the symmetry line is zero and structural stress components may be calculated by substituting $t_2=t/2$ and $\tau_{yx}=0$.

2.0. Calculation of Structural Stress by Conversion of Nodal Forces and Moments.

According to another embodiment of the present invention, structural stress $\sigma_s$ in a localized fatigue-prone region of a structure is also calculated. This embodiment of the present invention involves conversion of relevant nodal forces and moments, or internal force and moments at the nodes of a group of elements aligned with a weld toe line, to sectional forces and moments and may or may not involve a direct integration step similar to that described herein with reference to FIGS. 3-6.

As will be appreciated by those practicing the present invention, finite element models of a variety of structures have been, and may be, generated through computer-aided engineering. These finite element models may be used to derive individual stresses for an area of interest within the structure. Accordingly, the nodal forces and moments are typically derived from a finite element model and are described herein in the context of finite element models. It is important to note, however, that the nodal forces and moments may be derived or input from any of a variety of sources, either existing or yet to be developed. For example, a number of finite difference models and so-called meshless calculation systems are currently under development for structural modeling.

2.1. Conversion of Nodal Forces and Moments Retrieved Directly from Shell Model.

Figure 7:
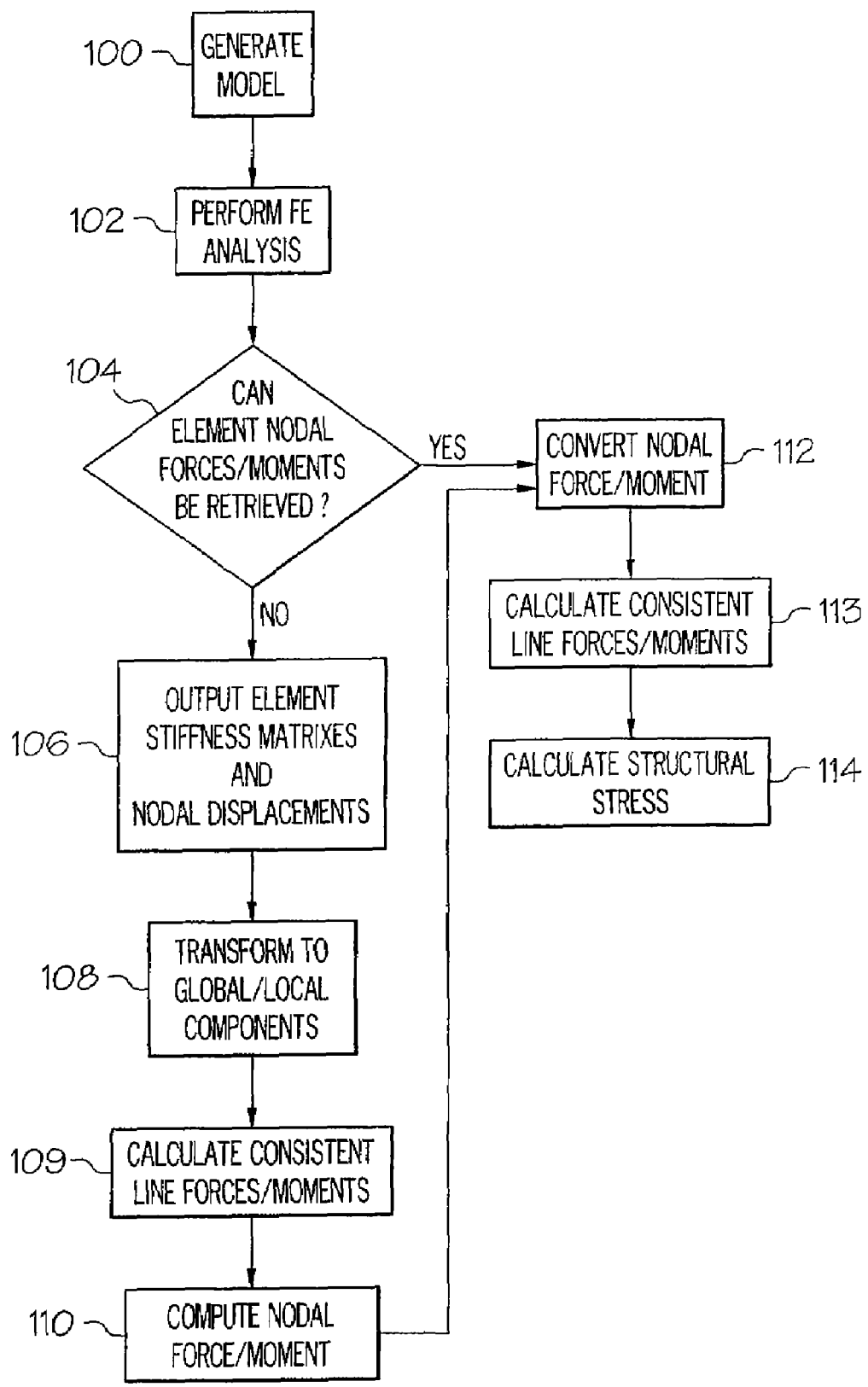
FIG. 7 is a flow chart illustrating a method of calculating structural stress for general three dimensional structures according to the present invention.
Figure 8:
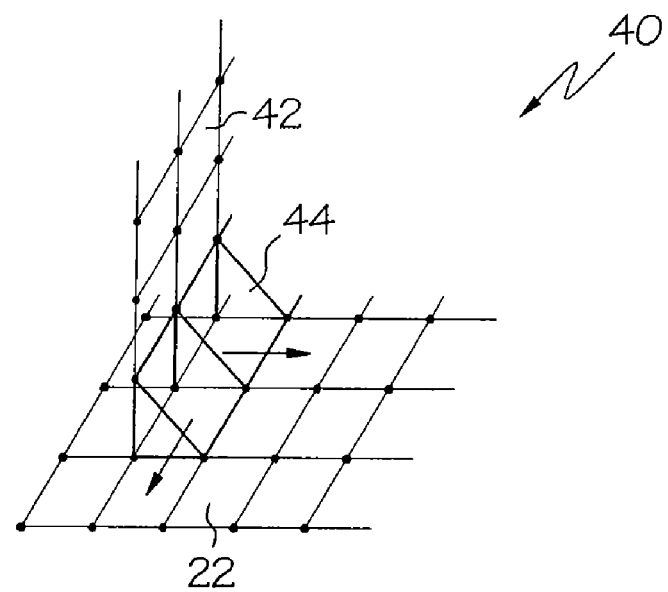
FIG. 8 illustrates a shell model and corresponding elements for structural stress extraction according to one embodiment of the present invention.

Specifically, referring to FIGS. 7 and 8, according to one aspect of the present invention, structural stress $\sigma_s$ in a localized fatigue-prone region of a structure is calculated from a finite element shell model of the structure. Typically, as is illustrated in FIG. 8, the structure and the welds are modeled with four-node (quadrilateral) shell or plate elements 42. Initially, a shell element model 40, see FIG. 8, of the structure at issue is generated utilizing a conventional computer aided engineering application (see step 100). Finite element analysis is performed on the shell element model (see step 102) and a determination is made as to whether nodal forces and moments for local elements of interest 42 can be directly retrieved from the output of the finite element analysis (see step 104). As is illustrated in FIG. 8, the elements 42 are positioned adjacent to a localized fatigue-prone region of a weld 44 and, as such, are identified for structural stress extraction. If the nodal force and moment vectors for the local elements 42 may be retrieved directly from the finite element shell model 40 then selected ones of the nodal force and moment vectors are converted to sectional force vectors n and moment vectors m with an appropriate mapping function that provides the consistent nodal loads, or work equivalent (see step 112). The conversion is performed in a work equivalent manner with respect to said nodal displacements determined for said nodal force and moment vectors (see step 113). Specifically, the conversion is performed such that a quantity of work corresponding to said nodal displacements and nodal force and moment vectors is equivalent to a quantity of work for said nodal displacements and said sectional force and moment vectors n and m.

The mapping function ideally should be the same as that used in the finite element program used in performing the structural analysis. The mapping function provides sectional forces (force per unit length) and moments (moment per unit length) corresponding to the nodal forces and moments. If high stress gradients exist, after mapping, the sectional forces and moments for a group of elements along the weld may not be continuous from one element to another. However, the total nodal forces and moments (as well as displacements) shared by neighboring elements at a nodal point or a grid point are correct from typical finite element solutions. The continuity in sectional forces and moments must be enforced by considering the neighboring elements and solving a system of linear equations formulated by using an appropriate mapping function for each element. The unknowns in the system of linear equations are sectional forces and moments at the nodes adjoining neighboring elements. The system of linear equations are formulated using nodal forces and moments (outputs from a finite element shell or plate models) and element geometric information. After solving the system of linear equations, the sectional forces and moments in the direction of interest can be used to calculate the structural stresses to be described below. If stress gradients along weld lines are not high and element shapes are not distorted, the structural stresses can be directly calculated on an element-by-element basis without resort to solving a system of linear equations, as discussed below with reference to the equation for structural stress $\sigma_s$.

Structural stress $\sigma_s$ in a localized fatigue-prone region of the structure may then be calculated according to the equation $$\sigma_s = \sigma_B + \sigma_M$$

where $\sigma_B$ is proportional to the sectional moment vector m and $\sigma_m$ is proportional to the sectional force vector n. More specifically, the structural stress as may be calculated utilizing the following equation:

$$\sigma_s = \sigma_B + \sigma_M = \frac{12mz}{t^3} + \frac{n}{t}$$

where t corresponds to the thickness of the structure in the fatigue-prone region and z ranges from +t/2 at the top surface of the structure to −t/2 at the bottom surface of the structure.

2.2. Conversion of Nodal Forces and Moments Using Stiffness Matrices and Nodal Displacements from the Shell Model.

In some applications, the reference section B-B in FIG. 10 may not be easily defined. This situation arises if welds are rather close to each other or load transfer at a weld of interest is very localized. If the element sectional forces and moments (with respect to the reference element in FIG. 10) at Section A-A are available from a finite element solution, the equilibrium requirements are automatically satisfied within the accuracy of the finite element solutions. In this context, if the nodal force and moment vectors can not be retrieved directly from the finite element model of the structure (see step 104) then the nodal force and moment vectors are computed by generating stiffness matrices and nodal displacements for the local elements in the fatigue-prone region from the finite element model (see step 106). The nodal force and moment vectors for elements of interest may then be computed by multiplying the stiffness matrices and nodal displacements to obtain global nodal force and moment vectors at nodal points of said local elements and transforming the resulting global force and moment vectors from the global coordinate system to the local coordinate system of an element of interest (see step 108). As is noted above, the transformation is performed in a work equivalent manner with respect to said nodal displacements (see step 109).

More specifically, the global stiffness matrix and nodal displacements may be used to determine local nodal force and moment vectors of an element of interest because the global element stiffness matrices and nodal displacements of the structure at issue are known (see step 110). The structural stress is calculated as follows:

$$\sigma_s = \sigma_M + \sigma_B = \frac{f_{x'}}{t} + \frac{6(m_{y'})}{t^2}$$

where t represents the dimensional value illustrated in FIG. 10 and $f_x$, and $m_y$, represent the stress resultants illustrated in FIG. 10.

It should be noted that, according to this aspect of the present invention, the finite element software used must allow for generation of the stiffness matrices and the nodal displacements for the elements of interest. It should also be noted that, since the element nodal forces and moments are based on finite element solutions, the transverse shear effects considered earlier in the context of two-dimensional solid models are already taken into account in the shell element approach.

2.3. Conversion of Nodal Forces and Moments from Three-Dimensional Solid Model.

Figure 9:
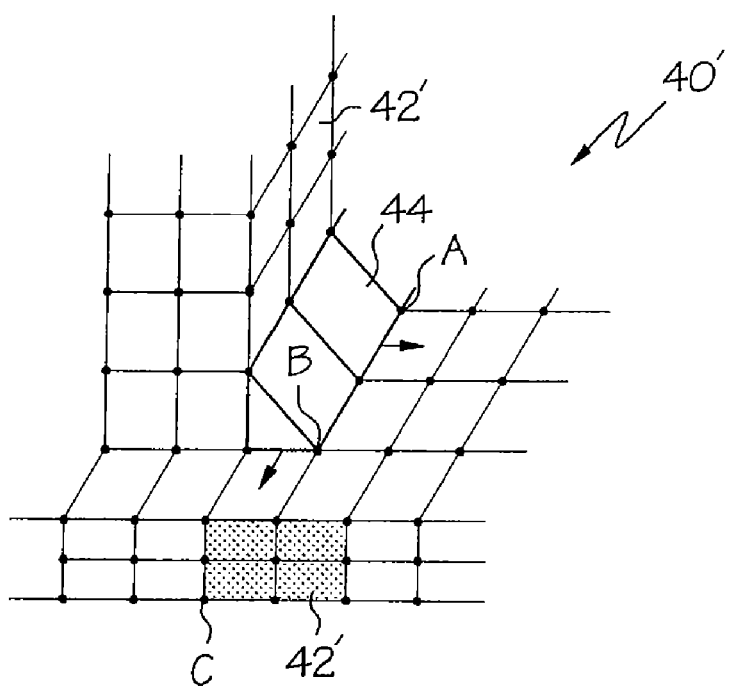
FIG. 9 illustrates a solid model and corresponding elements for structural stress extraction according to one embodiment of the present invention.

As is illustrated in FIG. 9, structural stress $\sigma_s$ in a localized fatigue-prone region of a structure may also be calculated from a finite element solid model of the structure by using nodal forces in a manner similar to that described above in the context of the shell/plate element models (see FIGS. 7 and 8). A general three dimensional finite element solid model 40' including local elements 42' and a weld 44 is illustrated in FIG. 9. A fatigue-prone plane of interest is illustrated along section A-B-C. Nodal forces on element faces can be either determined directly or through the local element stiffness matrix in a manner similar to that described in the context of FIG. 7. Once the nodal forces at the nodal positions are obtained, equivalent sectional forces and moments along Section A-B-C can then be obtained using consistent mapping or shape functions. The structural stress can then calculated with the equivalent sectional forces and moments in the manner described with reference to FIGS. 7 and 8. In addition, equivalent transverse shear effects need to be considered as discussed earlier with respect to the two-dimensional solid models.

It is contemplated that the various calculation schemes of the present invention are best performed with the aid of a computer programmed to execute the variety of calculation steps described herein or a computer arranged to read a suitable program stored on an appropriate recording medium.

3. Experimental Techniques for Measuring Structural Stress

Figure 12:
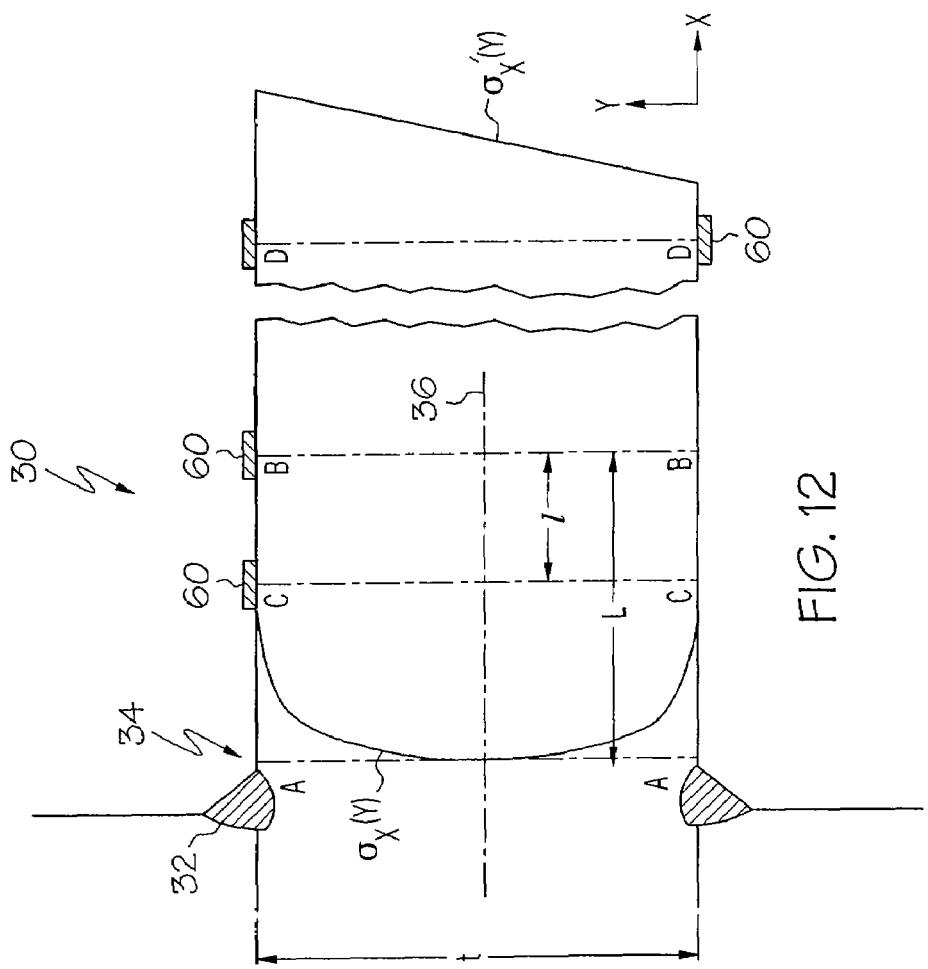
FIGS. 11 and 12 illustrate experimental techniques for measuring structural stress.
Figure 11:
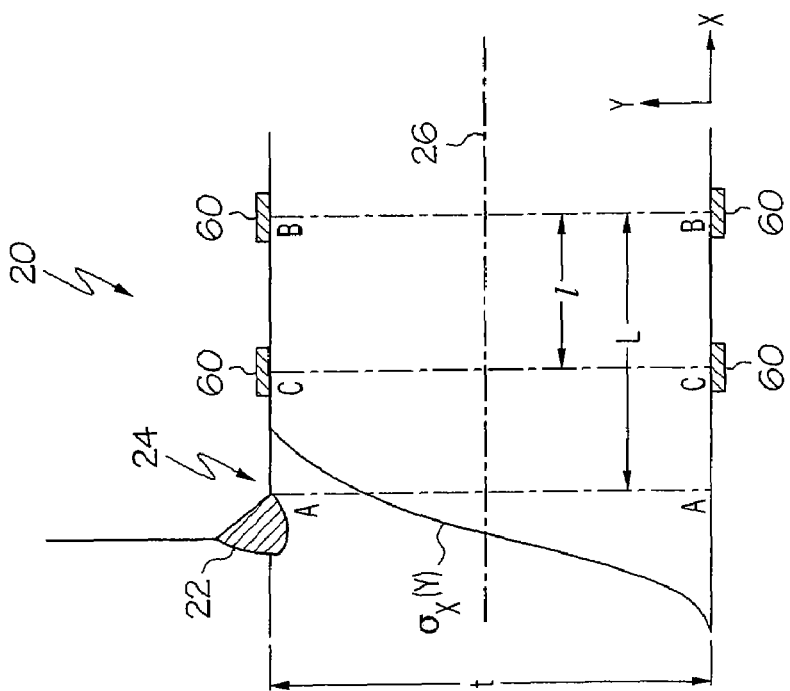

Referring now to FIGS. 11 and 12, it is noted that the structural stress calculation schemes of the present invention may also be utilized in fashioning experimental techniques for measuring structural stress by enforcing equilibrium conditions within a strip element adjacent to the weld toe of interest.

3.1. Monotonic Through-Thickness Distributions

FIG. 11 illustrates the local normal stress distribution $\sigma_x(y)$ of a structure 20 or, more specifically, a structural member 20, in a fatigue-prone region 24 in the vicinity of a weld 22 of the structure 20. The value of $\sigma_x(y)$ is taken along line A-A. The value of t corresponds to the thickness of the structure 20 in the selected cross section. The structural mid-plane 26 is illustrated in FIG. 11. Strain gauges 60, or other displacement measuring devices, are arranged along cross-sectional lines B-B and C-C.

Where through-thickness normal stress distributions take the form as shown in FIG. 11, stresses at the strain gauges can be calculated using strain gauge readings from measured positions along sections B-B and C-C. If the through-thickness stress distributions at the measured positions are approximately linear then the stress measurements can be decomposed as follows:

$$\sigma_b^B = \frac{1}{2}(\sigma_T^B - \sigma_B^B)$$

$$\sigma_b^C = \frac{1}{2}(\sigma_T^C - \sigma_B^C)$$

where the superscripts B and C indicate the sections at which the stresses are measured and subscripts T and B refer the values at the top and bottom surfaces, respectively. Linearity of the stress distributions at the measure positions can be readily confirmed by using one or more strain gauge readings, either at the top or bottom, to see if a linear distribution along the surface is developed.

The transverse shear resultant force effects at B-B, as described earlier in the context of finite element models, can be approximated by $$F_t = \frac{1}{l}\frac{I}{(t/2)}(\sigma_b^C - \sigma_b^B)$$

where I is the moment of inertia of the structural member 20. If the distance between sections A-A and C-C is small, the increase in the bending stress component at section A-A can be approximated as:

$$\sigma_b = \sigma_b^B + \frac{L}{l}(\sigma_b^C - \sigma_b^B)$$

The structural stress, as defined previously in FIG. 4, can then be approximated based on the measurements at sections B-B and C-C as:

$$\sigma_S = \sigma_T^B + \frac{L}{l}(\sigma_b^C - \sigma_b^B)$$

The distances among sections A-A, B-B, and C-C are typically measured in terms of fractions of thickness t.

3.2. Non-Monotonic Through-Thickness Stress Distributions

Referring now to FIG. 12, it is noted that non-monotonic stress distributions can be handled in a manner similar to that described above with reference to FIG. 11. FIG. 12 illustrates the local normal stress distribution $\sigma_x(y)$ of a structure 30 or, more specifically, a structural member 30, in a fatigue-prone region 44 in the vicinity of a weld 32 of the structure 30. The value of $\sigma_x(y)$ is taken along line A-A. The value of t corresponds to the thickness of the structure 30 in the selected cross section. The structural mid-plane 36 is illustrated in FIG. 11. Strain gauges 60 are arranged along cross-sectional lines B-B, C-C, and D-D.

Measurements at section D-D, where the stress distribution $\sigma_x(y)'$ becomes approximately linear, provide the through-thickness mean stress $\sigma_m$ as follows:

$$\sigma_m = \frac{(\sigma_T^D + \sigma_B^D)}{2}$$

Typically, $\sigma_m$=F/A (load F and cross-sectional area A are typically available). Accordingly, the structural stress component $\sigma_M$, as defined in FIG. 6C, becomes $\sigma_M$=$\sigma_m$ and $$\sigma_b^B = \sigma_T^B - \sigma_m$$

$$\sigma_b^C = \sigma_T^C - \sigma_m$$

The structural stresses with respect to the upper half of the thickness (as shown in FIG. 6C) can be approximated as:

$$\sigma_S = \sigma_T^B + \frac{L}{l}(\sigma_b^C - \sigma_b^B)$$

It is noted that general monotonic and symmetric stress distributions can be handled in a manner to that illustrated in FIGS. 11 and 12, with the exception that $t_2$ and the corresponding appropriate equilibrium conditions must be accounted for in the manner discussed above with respect to FIG. 6C. A structure including a partial thickness fatigue crack, as illustrated with reference to FIGS. 5A-5C above, can also be treated with a technique similar to that illustrated with reference to FIG. 11, as long as the two strain gauges 60 utilized at the bottom of the structure 20 (see FIG. 11) are positioned a distance $t_1$ from the top edge (see FIG. 5B). The specific calculation procedures are then the same as those illustrated with reference to the monotonic through-thickness distribution case of FIG. 11.

It is also noted that the present application discusses conventional strain gauges as a suitable means for measuring displacement/strain merely for the purposes of illustrating the present invention. It is contemplated that a variety of displacement/strain measurement devices may be employed according to the present invention including, but not limited to, imaging devices, laser-based devices, fiber-optic gauges, ultrasonic gauges, etc.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

As will be appreciated by those practicing the present invention, it is possible to utilize alternatives to the selected integrations described in detail herein. Indeed, any mathematical or procedural operation that has a result that is substantially equivalent to the result of a selected integration may be performed according to the present invention. For the purpose of defining the present invention, a claim recitation of an operation having a result substantially equivalent to a result of a given integration reads on the integration itself and the equivalent operation.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of analyzing structural stress $\sigma_s$ in a fatigue-prone region of a structure, said method comprising:
    determining a stress distribution $\sigma_x$ (y) along a selected cross section of said structure;
    determining a first component $\sigma_M$ of said structural stress $\sigma_s$ in said fatigue-prone region by performing an operation having a result substantially equivalent to a result of the following first integration $$\sigma_M = \frac{1}{t}\int_0^t \sigma_x(y)\,dy$$

where $\sigma_x(y)$ represents a through-thickness stress distribution and t corresponds to a thickness of said structure;
    determining a second component $\sigma_B$ of said structural stress $\sigma_s$ in said fatigue-prone region by performing an operation having a result substantially equivalent to a solution of the following equation for $\sigma_B$ $$\left(\frac{t^2}{2}\right)\sigma_M + \left(\frac{t^2}{6}\right)\sigma_B = \int_0^t \sigma_x(y)y\,dy$$

or, its mathematical equivalent $$\sigma_B = \frac{6}{t^2}\int_0^t \sigma_x(y)\left(y - \frac{t}{2}\right)dy$$

where y corresponds to a position along said selected cross section, t corresponds to said thickness of said structure, and $\sigma_x(y)$ represents said through-thickness stress distribution; and
    calculating said structural stress $\sigma_s$ by combining said first component $\sigma_M$ of said structural stress and said second component $\sigma_B$ of said structural stress.

2. A method of analyzing structural stress as claimed in claim 1 wherein said second component $\sigma_B$ of said structural stress $\sigma_s$ in said fatigue-prone region is determined by solving the following equation for $\sigma_B$ $$\left(\frac{t^2}{2}\right)\sigma_M + \left(\frac{t^2}{6}\right)\sigma_B = \int_0^t \sigma_x(y)y\,dy.$$

3. A method of analyzing structural stress as claimed in claim 1 wherein said second component $\sigma_B$ of said structural stress $\sigma_s$ in said fatigue-prone region is determined by solving the following equation for $\sigma_B$ $$\sigma_B = \frac{6}{t^2}\int_0^t \sigma_x(y)\left(y - \frac{t}{2}\right)dy.$$

4. A computer-readable medium encoded with a computer program for analyzing structural stress $\sigma_s$ in a fatigue-prone region of a structure according to the method of claim 1.

5. A system for analyzing structural stress $\sigma_s$ in a fatigue-prone region of a structure according to the method of claim 1.

6. A method of analyzing structural stress $\sigma_s$ in a fatigue-prone region of a structure, said method comprising:
- determining a stress distribution $\sigma_x(y)$ along a selected cross section of said structure;
- determining a first component $\sigma_M$ of said structural stress $\sigma_s$ in said fatigue-prone region by performing an operation having a result substantially equivalent to a result of the following first integration $$\sigma_M = \frac{1}{t}\int_0^t \sigma_X(y)\,dy$$

where $\sigma_x(Y)$ represents a through-thickness stress distribution and t corresponds to a thickness of said structure;
- determining a second component $\sigma_B$ of said structural stress $\sigma_s$ in said fatigue-prone region by performing an operation having a result substantially equivalent to a solution of the following equation for $\sigma_B$ $$\left(\frac{t^2}{2}\right)\sigma_M + \left(\frac{t^2}{6}\right)\sigma_B = \int_0^t \sigma_X(y)\,y\,dy + \delta\int_0^t \tau_{xy}(y)\,dy$$

where y corresponds to a position along said selected cross section, t corresponds to said thickness of said structure, $\delta$ is a value defined in said representation of said structure, $\sigma_x(Y)$ represents said through-thickness stress distribution, and $\tau_{xy}(y)$ represents a through-thickness shear stress distribution of said structure; and
- calculating said structural stress $\sigma_s$ by combining said first component $\sigma_M$ of said structural stress and said second component $\sigma_B$ of said structural stress.

7. A computer-readable medium encoded with a computer program for analyzing structural stress $\sigma_s$ in a fatigue-prone region of a structure according to the method of claim 6.

8. A system for analyzing structural stress $\sigma_s$ in a fatigue-prone region of a structure according to the method of claim 6.

9. A method as claimed in claim 1, further comprising manufacturing a structure utilizing the calculated structural stress $\sigma_s$.

10. A method as claimed in claim 9, wherein the structure comprises welded and non-welded joints, notches, ridges, bends, sharp corners, or discontinuities or sudden changes in geometry.

11. A method as claimed in claim 9, wherein the structure comprises a metallic, plastic, or ceramic structure.

12. A method as claimed in claim 9, wherein the structure is selected from the group consisting of aircraft or aerospace equipment, agricultural equipment, agricultural structures, automobiles or trucks, construction or lifting equipment, forestry equipment, minimg equipment, rail car frames, ships, submarines and submersibles; ports and port equipment, bridges, channels or canals, tunnels, building components, building materials, appliances, buildings/skyscrapers, housing, heating and cooling systems, home improvement equipment, fencing and gates, plumbing, irrigation and drainage equipment, manufacturing equipment and machinery, diving equipment, nuclear containers and facilities, offshore oil rigs, diesel and gas turbines, pipelines, derricks and digger derricks, cooling towers, radio towers/transmitters, welded structures, tanks and cisterns, automotive parts, footwear, household components, sporting goods, ceramics, concrete, porcelain enamel, sealants and sealed structures, adhesively bonded structures, and components thereof.

13. A method as claimed in claim 6, further comprising manufacturing a structure utilizing the calculated structural stress $\sigma_s$.

14. A method as claimed in claim 13, wherein the structure comprises welded and non-welded joints, notches, ridges, bends, sharp corners, or other discontinuities or sudden changes in geometry.

15. A method as claimed in claim 13, wherein the structure comprises a metallic, plastic, or ceramic structure.

16. A method as claimed in claim 13, wherein the structure is selected from the group consisting of aircraft or aerospace equipment, agricultural equipment, agricultural structures, automobiles or trucks, construction or lifting equipment, forestry equipment, minimg equipment, rail car frames, ships, submarines and submersibles; ports and port equipment, bridges, channels or canals, tunnels, building components, building materials, appliances, buildings/skyscrapers, housing, heating and cooling systems, home improvement equipment, fencing and gates, plumbing, irrigation and drainage equipment, manufacturing equipment and machinery, diving equipment, nuclear containers and facilities, offshore oil rigs, diesel and gas turbines, pipelines, derricks and digger derricks, cooling towers, radio towers/transmitters, welded structures, tanks and cisterns, automotive parts, footwear, household components, sporting goods, ceramics, concrete, porcelain enamel, sealants and sealed structures, adhesively bonded structures, and components thereof.

\* \* \* \* \*

UNITED STATES PATENT AND TRADEMARK OFFICE
CERTIFICATE OF CORRECTION

PATENT NO. : 7,516,673 B2
APPLICATION NO. : 11/424404
DATED : April 14, 2009
INVENTOR(S) : Dong et al.

It is certified that error appears in the above-identified patent and that said Letters Patent is hereby corrected as shown below:

Col. 7, Line 4 "structural stress as in the localized region" should read --structural stress $\sigma_S$ in the localized region--;

Col. 7, Line 17 "structural stress as in the localized region" should read --structural stress $\sigma_S$ in the localized region--;

Col. 10, Line 5 "$\sigma_S = \sigma_M + v_B$" should read --$\sigma_S = \sigma_M + \sigma_B$--;

Col. 10, Line 19 "$t_2 = t/2$ ;" should read --$t2 = t/2$--;

Col. 12, Line 19 "structural stress as may be calculated" should read --structural stress $\sigma_S$ may be calculated--;

Col. 17, Line 15 "where $\sigma_x(Y)$ represents" should read --where $\sigma_x(y)$ represents--;

Col. 17, Line 30 "where $\sigma_x(Y)$ represents" should read --where $\sigma_x(y)$ represents--;

Col. 17, Line 47 "or discontinuities" should read --or other discontinuities--;

Col. 18, Line 7 "minimg" should read --mining--; and

Col. 18, Line 16 "minimg" should read --mining--.

Signed and Sealed this

Eighteenth Day of August, 2009

David J. Kappos
*Director of the United States Patent and Trademark Office*